(12) United States Patent
Bromwich et al.

(10) Patent No.: US 9,119,574 B2
(45) Date of Patent: Sep. 1, 2015

(54) HEARING SCREENING APPLICATION FOR MOBILE DEVICES

(75) Inventors: Matthew Bromwich, Ottawa (CA); Guy-Vincent Jourdan, Ottawa (CA); Nicolas Ellaham, Ottawa (CA)

(73) Assignees: The University of Ottawa, Ottawa (CA); The Children's Hospital Of Eastern Ontario, Ottawa (CA)

( * ) Notice: Subject to any disclaimer, the term of this patent is extended or adjusted under 35 U.S.C. 154(b) by 323 days.

(21) Appl. No.: 13/598,762

(22) Filed: Aug. 30, 2012

(65) Prior Publication Data

US 2013/0060159 A1    Mar. 7, 2013

Related U.S. Application Data

(60) Provisional application No. 61/530,178, filed on Sep. 1, 2011.

(51) Int. Cl.
*A61B 5/00* (2006.01)
*A61B 5/12* (2006.01)

(52) U.S. Cl.
CPC . *A61B 5/12* (2013.01); *A61B 5/123* (2013.01); *A61B 5/6898* (2013.01)

(58) Field of Classification Search
None
See application file for complete search history.

(56) References Cited

U.S. PATENT DOCUMENTS

| 4,862,505 A * | 8/1989 | Keith et al. | 381/60 |
| 6,496,585 B1 | 12/2002 | Margolis | |
| 7,704,216 B2 | 4/2010 | Margolis | |
| 2003/0083591 A1 | 5/2003 | Edwards et al. | |
| 2004/0006283 A1 * | 1/2004 | Harrison et al. | 600/559 |
| 2004/0073136 A1 * | 4/2004 | Thornton et al. | 600/559 |
| 2007/0135730 A1 * | 6/2007 | Cromwell et al. | 600/559 |
| 2008/0049946 A1 * | 2/2008 | Heller et al. | 381/60 |
| 2009/0060214 A1 * | 3/2009 | Wessel et al. | 381/60 |
| 2010/0191143 A1 * | 7/2010 | Ganter et al. | 600/559 |

FOREIGN PATENT DOCUMENTS

WO    WO2010/139760    12/2010

OTHER PUBLICATIONS

American Speech-Language-Hearing Association "Guidelines for Manual Pure-Tone Threshold Audiometry" Guidelines (2005).
B. McPherson et al "Hearing Screening for School Children: Comparison of Low-Cost, Computer-Based and Convention Audiometry" Child: care, health and development (2010).

* cited by examiner

*Primary Examiner* — Brian Szmal
*Assistant Examiner* — Matthew Kremer
(74) *Attorney, Agent, or Firm* — Harness, Dickey & Pierce, P.L.C.

(57) ABSTRACT

A computer-implemented method is provided for conducting a hearing assessment of a patient. The method includes: presenting a plurality of objects on a display of a computing device, where each object produces an audio output in response to a stimuli from the patient and the audio output by the objects varies in frequency and intensity amongst the plurality of objects; prompting a patient with a visual cue to classify objects producing sound; receiving an input from the patient for each object in the plurality of objects, where the input indicates whether the audio output by a given object was perceptible to the patient; and generating an audiogram for the patient using the input received from the patient.

12 Claims, 8 Drawing Sheets

HEARING SCREENING APPLICATION FOR MOBILE DEVICES

CROSS-REFERENCE TO RELATED APPLICATIONS

This application claims the benefit of U.S. Provisional Application No. 61/530,178, filed on Sep. 1, 2011. The entire disclosure of the above application is incorporated herein by reference.

FIELD

The present disclosure relates to improved techniques for conducting hearing assessments, for example of children.

BACKGROUND

Timely diagnosis of hearing loss in children has significant implications for a child's social and cognitive development. In young children, hearing loss is often inconspicuous resulting in delayed diagnosis and rehabilitation. As a result, children are at increased risk of delayed speech acquisition and the subsequent long-term sequelae. Speech delay and hearing loss also represents a significant cost to society due to the resources required for their treatment, such as special education, speech therapy, and social services. However, it is clear that early detection is the key to restoring normal speech development and a favorable long-term outcome.

Definitive diagnosis of hearing loss is typically made through audiologic assessment of pure-tone air, bone and speech thresholds. Traditionally, pure-tone thresholds are documented by asking the subject if they can hear tones of varying frequency and intensity. Currently, standard clinical audiometry is performed using expensive, proprietary, non-portable hardware and access is therefore limited in developing countries, where hearing loss is more prevalent.

Automation of pure-tone audiometry offers several potential benefits. Particularly, a portable, automated audiometer improves accessibility, creating the possibility of routine pure-tone audiometry in the primary care setting or in remote communities. Such a device may eventually permit a parent or teacher access to screening audiometry, resulting in earlier detection of hearing impairment. However, there may be significant differences between mean hearing thresholds determined though automated audiometry and manual audiometry. As such, clinical validation of any automated audiometer is a necessity.

Pure-tone audiometry, regardless of automation or lack thereof, is a mundane task. It is especially challenging to perform in the pediatric population where short attention span and the extent of cognitive development can be limiting factors. Children with hearing impairment may find audiometric testing even more difficult. Several adaptations of pure-tone audiometry are used to evaluate hearing in children. These techniques include behavioral observation, visual re-enforcement, and conditioned play audiometry. While more successful than conventional pure-tone audiometry, these adaptations are resource intensive and typically require two specially trained audiologists to administer. Naturally, an ideal solution would capitalize on the advantages of automation, while maintaining clinical validity and age appropriateness.

This section provides background information related to the present disclosure which is not necessarily prior art.

SUMMARY

A computer-implemented method is provided for conducting a hearing assessment of a patient. The method includes: presenting a plurality of objects on a display of a computing device, where each object produces an audio output in response to a stimuli from the patient and the audio output by the objects varies in frequency and intensity amongst the plurality of objects; prompting a patient with a visual cue to classify objects producing sound; receiving an input from the patient for each object in the plurality of objects, where the input indicates whether the audio output by a given object was perceptible to the patient; and generating an audiogram for the patient using the input received from the patient. The audiogram may include a threshold of hearing for the patient at a given frequency using input received from the patient in the relation to the presented objects.

The method further includes presenting the objects such that each object in the sequence produces an audio output at a first frequency and a given object is not presented until a previously presented object is classified by the patient. Additionally, the intensity of the audio output may be varied by increasing intensity of the audio output between each object in the sequence of objects at a predefined increment until the audio output is deemed audible by the patient and then decreasing intensity of the audio output between each object in the sequence of objects at a defined increment until the audio output is deemed inaudible by the patient.

The method may further include presenting a second set of objects sequentially such that each object in the sequence produces an audio output at a second frequency different than the first frequency and a first object in the second set of objects producing an audio output having an intensity equal to the threshold of hearing for the patient at the first frequency.

In another aspect of this disclosure, a hearing assessment application is presented for conducting a hearing assessment of a patient using a mobile computing device. The hearing assessment application is comprised generally of a presentation manager, a protocol manager and a controller. The presentation manager is configured to present a first set of objects sequentially on a display of the mobile computing device as well as receive an input from the patient for each object presented from the first set of objects, where each object in the first set of objects produces an audio output at a first frequency in response to a stimuli from the patient and intensity of the audio output varies amongst the object presented from the first set of objects. The protocol manager determines an intensity value for the audio output produced by objects in the first set of objects in accordance with a medical testing protocol. The controller is configured to receive the intensity value for audio output produced by objects in the first set of objects and determine a threshold of hearing for the patient at the first frequency using the input received from the patient in the relation to the first set of objects.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
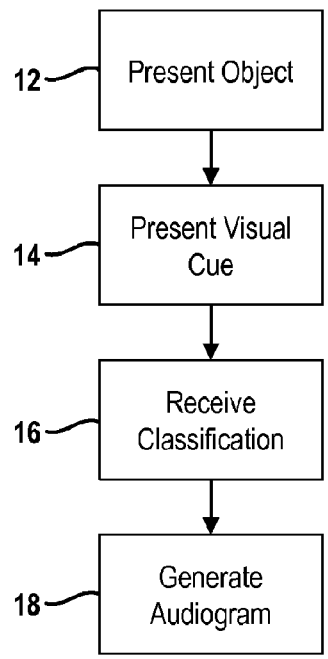
FIG. 1 is a flowchart depicting an exemplary paradigm for conducting a hearing assessment.

FIG. 1 illustrates a novel paradigm for a hearing assessment application 10 residing on a mobile computing device. In this paradigm, the patient controls the presentation and pace of sound stimuli, rather than the audiologist. The patient is presented at 12 with a series of objects on a display of a computing device. Each object produces an audio output in response to a stimuli from the patient, where the audio output varies in frequency and intensity amongst the different objects. For example, the object produces an audio input when the patient touches the object being presented on a touchscreen, thereby controlling the pace of sound stimuli.

The patient may also be prompted at 14 with a visual cue to classify the sound-producing objects. For example, the patient is presented one container for objects whose sound is audible to the patient and another container for objects whose sound is inaudible to the patient. The task is to classify the objects by dragging the objects into one of the two containers. In this way, input is received at 16 from the patient for each of the presented objects, where the input indicates whether the audio output for a given object was perceptible to the patient. It is noted that the visual cue is preferably displayed concurrently with the sound producing objects.

Figure 2:
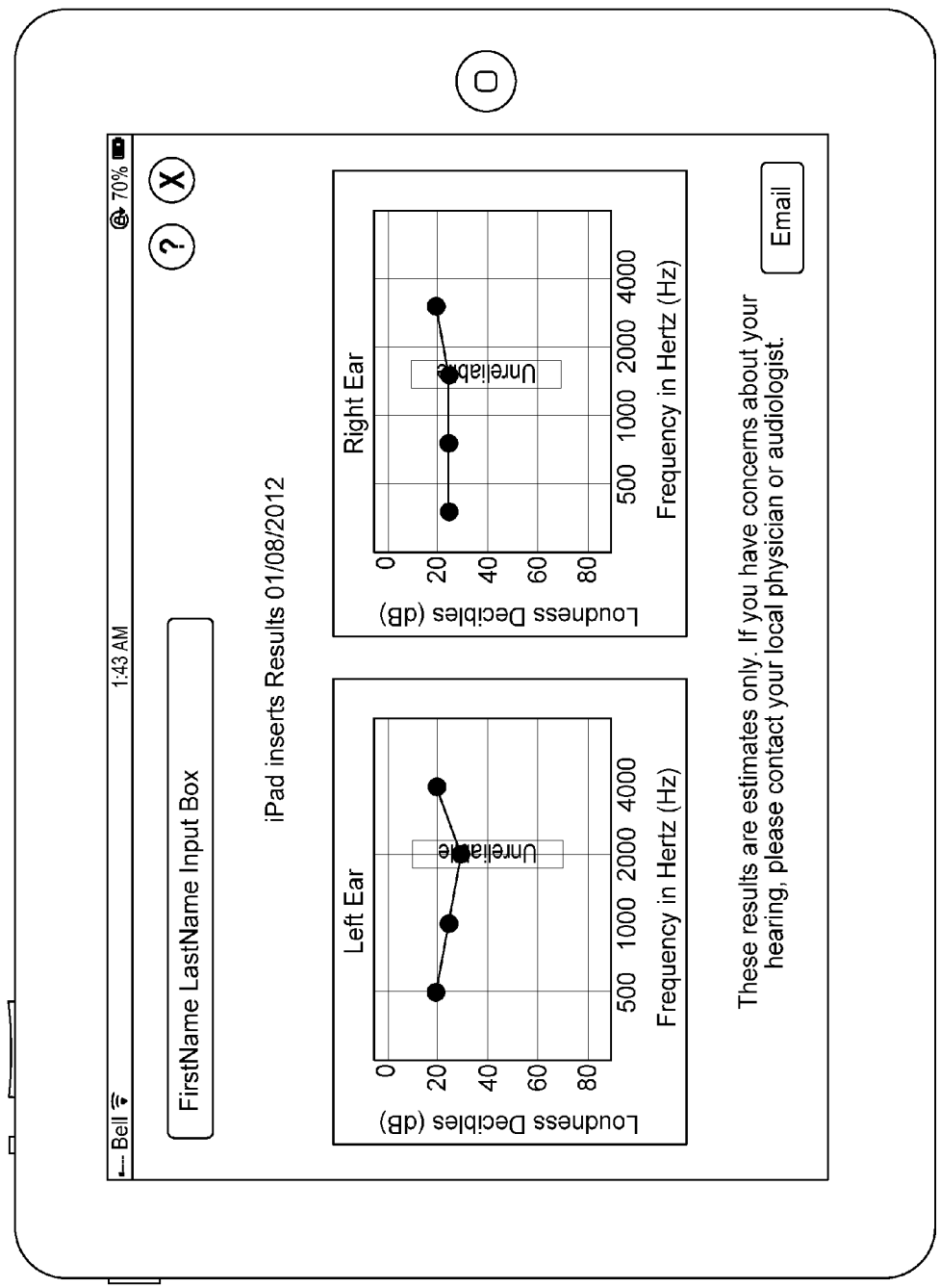
FIG. 2 is an illustration of an exemplary audiogram.

Once the series of objects have been presented to the patient, an audiogram is generated at 18 for the patient using the input received from the patient. The audiogram can then be displayed on a user interface of a computing device as shown in FIG. 2. In this example, an audiogram is presented for each ear of the patient. The audiogram indicates the threshold of hearing for each frequency at which the patient was tested. The user interface may provide the capability of sending the audiogram to a designated recipient, for example a treating physician. In other examples, the audiogram may be generated and stored on the computing device but a simplified outcome is presented on the user interface to the patient. For example, the patient is presented with a message such as "this assessment did not detect any problems with your hearing" or "this assessment has detect a concern about your hearing, please contact your physician or audiologist for further testing". Other types of outputs are contemplated by this disclosure.

Figure 3A:
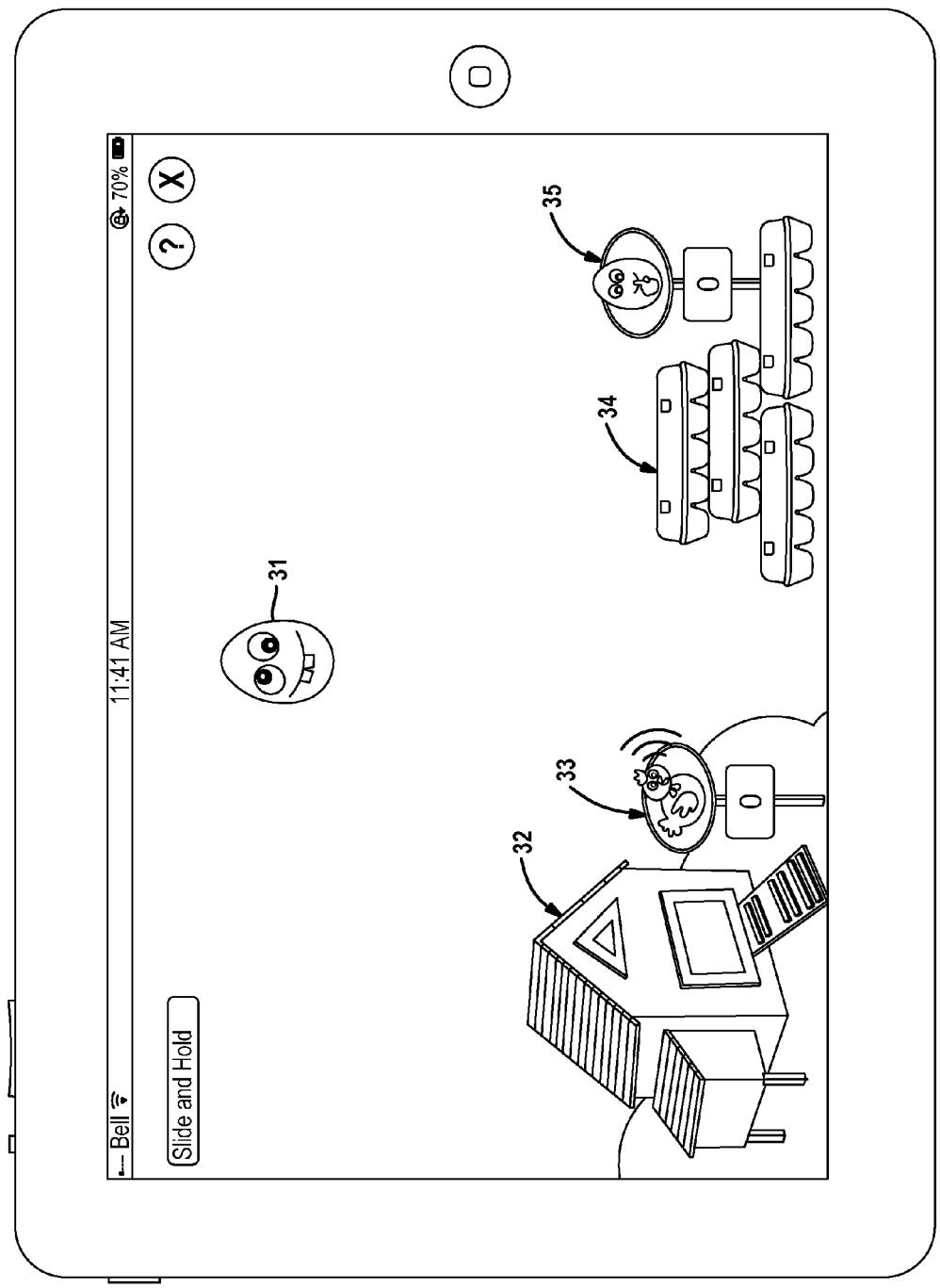
FIGS. 3A-3C are diagrams of an exemplary user interface for the hearing assessment application.
Figure 3B:
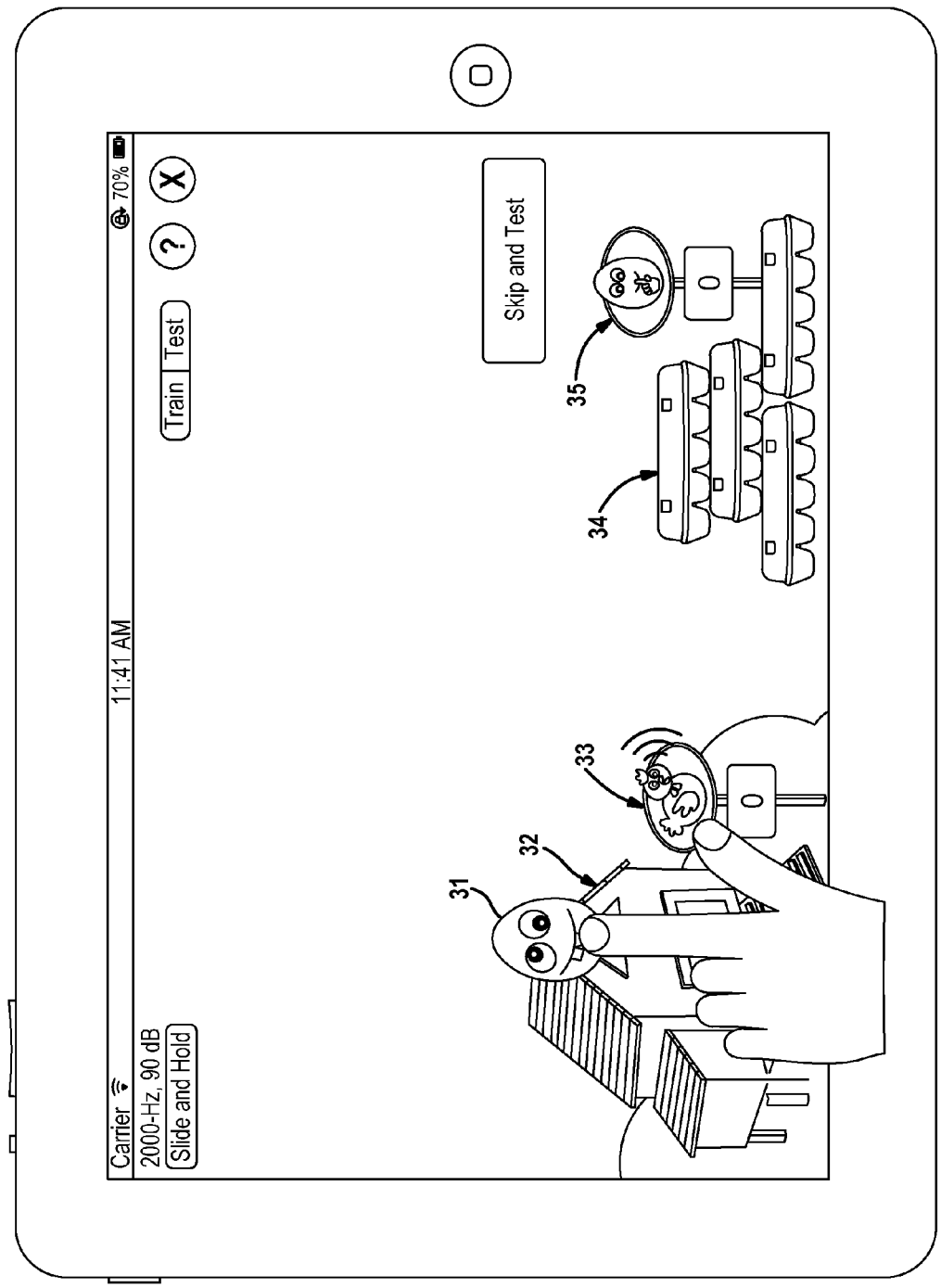
Figure 3C:
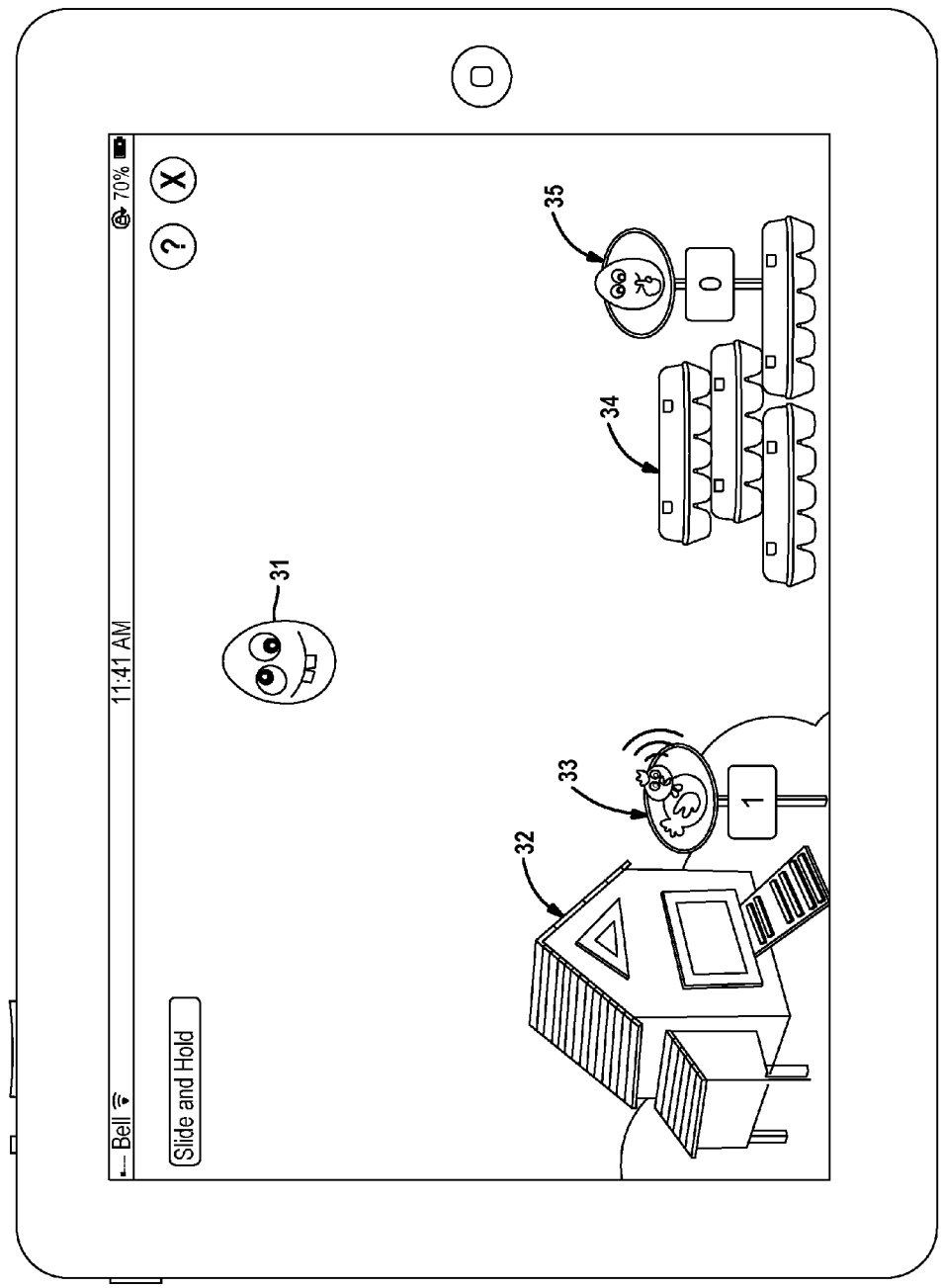

FIGS. 3A-3C illustrate an exemplary embodiment of a user interface for conducting the hearing assessment. In the exemplary embodiment, a forced choice yes/no paradigm is the psychophysical method used to elicit responses from the patient. The patient is presented sequentially with a series of eggs. The task is to drag the eggs to either a chicken coop or an egg carton. Each egg as indicated at 31 will produce sound in response to a stimuli, for example, being touched on a touchscreen or otherwise selected (e.g., a mouse click) by the patient. With reference to FIG. 3B, eggs producing sound that is audible to the patient are to be dragged to the chicken coop 32; whereas, eggs producing sound that is inaudible to the patient are to be dragged to the egg carton 34. Visual cues are provided to help the patient classify the objects. In this example, a clucking chicken 33 is displayed next to the chicken coop 32 and a hushing egg 35 is displayed next to the egg cartons 34. Once an egg has been classified by the patient, another egg is presented to the patient. In this game, the patient is essentially navigating his/her own test and responding in a yes/no fashion to each stimulus. The patient is not presented with an option for "I don't know" or "not sure".

Figure 4:
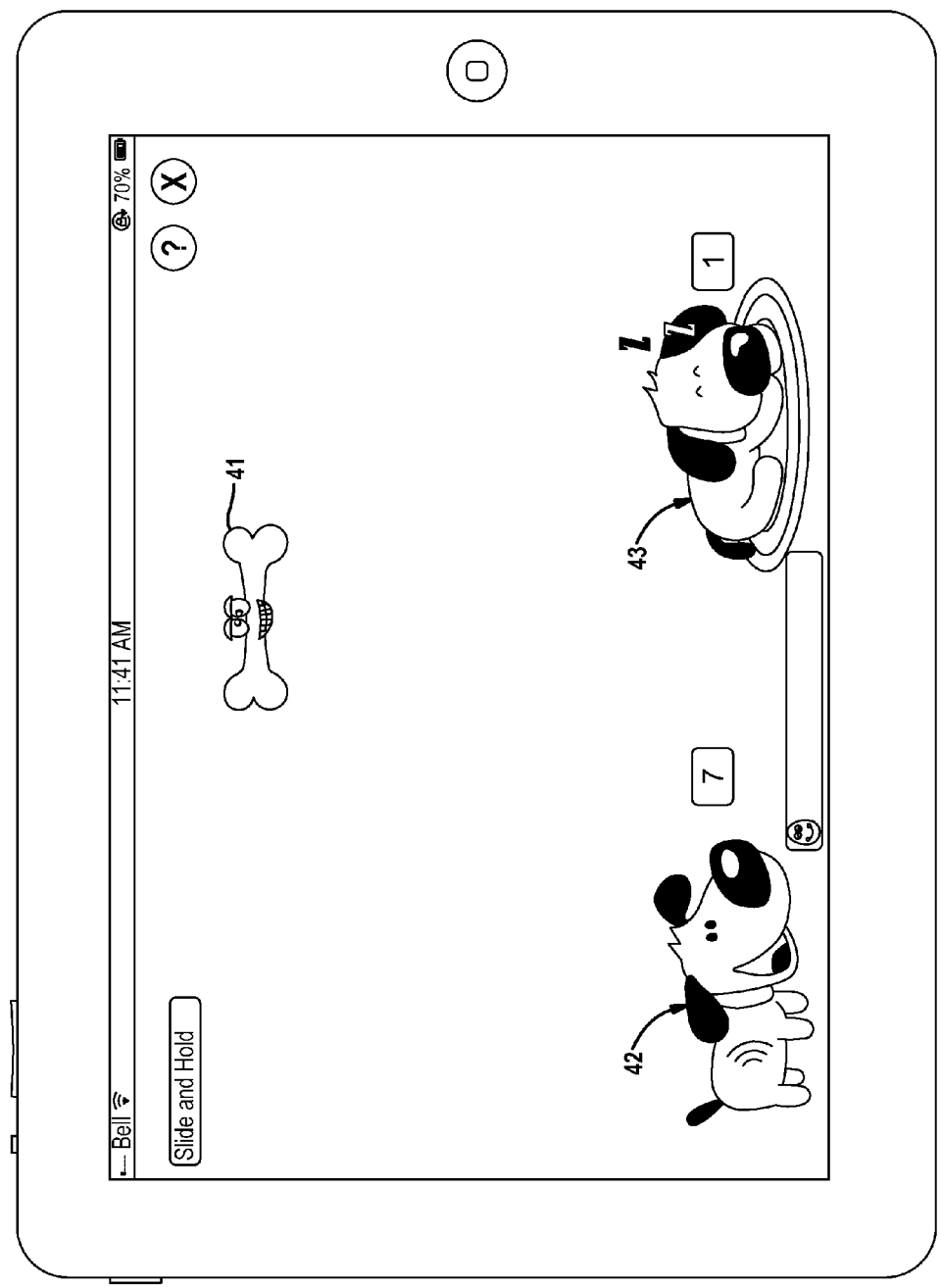
FIG. 4 is a diagram of another exemplary user interface for the hearing assessment application.

Different types of game scenarios are envisioned. For example, the patient may be presented sequentially with a series of bones as shown in FIG. 4. In this case, the task is to drag the bone 41 to either the barking dog 42 or the sleeping dog 43. Bones producing sound that is audible to the patient are to be dragged to the barking dog 42; whereas, bones which produce sound that is inaudible the patient are to be dragged to the sleeping dog 43. In another example, the patient is presented with three different objects concurrently, where only one of the objects produces sound in response to a stimuli from the patient and the other two objects remain silent. In this example, the patient must first identify the object that produces sound and then classify the object as in the other game scenarios.

Younger children may have difficulty understanding the sorting concept of the forced choice yes/no paradigm. In a simplified variant, the patient is presented with only one container and the task is to drag objects into this container if it produces sound. Objects that are not dragged into the container (i.e., objects producing sound that is inaudible to the patient) can be removed from the display a predetermined period of time (e.g., 3 seconds) after being stimulated by the patient. Other types of gaming scenarios will be readily apparent from these examples.

In the exemplary embodiment, the sound-producing object produces a unique tone (e.g., a pure tone or warble tone) at 500, 1000, 2000 or 4000 Hertz although more or less frequencies may be tested. A first object produces a sound at a predefined intensity, for example 60 decibels. For each subsequent object, the intensity of the sound may decrease with each presentation until the patient is unable to reproducibly sort the objects. The intensity of the sounds is subsequently increased. Thresholds of hearing are determined in accordance with standard medical protocols, for example, by the Hughson-Westlake method. Once a threshold has been established at a given frequency, objects that produce sounds at a different frequency are presented to the patient. The process is repeated until a threshold has been established across a range of predefined frequencies.

In a variant, the hearing threshold is found following a bracketing technique (e.g. up by 10 dB until heard, down by 5 dB until not heard, twice) but the initial phase is sped up in two ways. For the first frequency, the variant protocol goes from a fairly high presentation level (e.g. 60 dB) to a fairly low one (e.g. 20 dB) in just two steps, testing only the presentation level in between (e.g. 40 dB in the case) on the way. The bracketing starts at the lowest presentation level successfully heard. For the other frequencies, the bracketing starts at the previous hearing threshold for the same ear. Other variants to the bracketing technique are also contemplated by this disclosure.

Audiometric tests are preferably performed using pure tone signals as noted above. In free field, these signals create standing waves which result in a non-uniform sound intensity across the sound field. This, coupled with unpredictable listener movements, makes pure tone signals not suitable for use in a hearing assessment application. The ASHA guidelines recommend using frequency-modulated (FM) tones with carrier frequency, modulation rate and bandwidth as detailed by Walker et al in "Sound field audiometry: Recommended stimuli and procedures", Ear and Hearing 5, 13-21 (1984). In the exemplary embodiment, specifications for wide bandwidth were chosen for the stimuli used in this hearing assessment application, thus favouring sound-field uniformity over audiometric accuracy.

In some embodiments, silent objects may be randomly presented to the patient. Silent objects do not produce any sound. The silent objects are used as a measure of consistency or reliability. If a silent object is misclassified by the patient, the assessment may invoke some corrective action. For example, the patient may be presented with a demonstration of how objects are to be classified. Additionally or alternatively, earlier portions of the assessment may be repeated or the patient may be administered a different type of hearing assessment.

Figure 5:
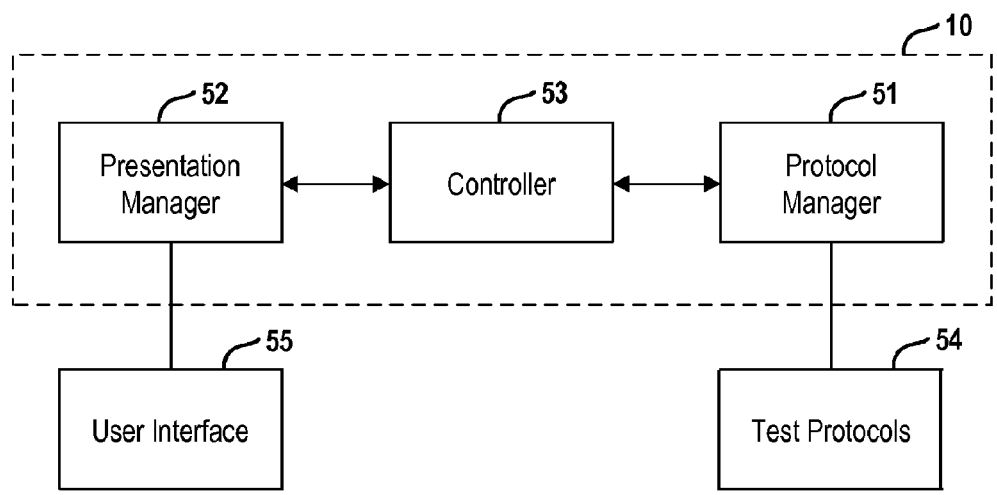
FIG. 5 is a block diagram depicting an exemplary construct for the hearing assessment application.

FIG. 5 depicts an exemplary construct for the hearing assessment application 10. The hearing assessment application 10 is comprised generally of a protocol manager 51, a presentation manager 52 and a controller 53. Each of these components is further described below.

In an exemplary embodiment, the protocol manager 51 is primarily responsible for determining the hearing threshold of the patient. To achieve this, it can administer any suitable medical protocol, e.g. the standard Hughson-Westlake method noted above. The protocol manager 51 communicates with the controller 53, indicating what presentation level (i.e., sound intensity) to test next. Once a test is done, the controller 53 tells the protocol manager 51 what the result was (success or failure) and the protocol manager 51 uses this result to decide what to do next and whether or not a hearing threshold has been established for a given frequency.

The presentation manager 52 manages the user interface presented to the patients and their interactions therewith. During operation, the presentation manager 52 receives a "sound" to test (i.e., frequency and intensity) from the protocol manager 51 and in turn implements the test, for example by presenting a suitable object on the user interface. Upon receipt of the patient input, the presentation manager 52 reports the patient input to the controller 53. The presentation manager 52 is a generic software component that can be implemented on the user interface in a number of ways, from a simple "clicker" that the patient pushes when a sound is heard to a more robust game scenario as described above in connection with FIGS. 3 and 4. The presentation manager 52 provides the ability to adapt the presentation to the skills and interest of the patient, including the ability to change the user interface during the hearing assessment test.

The controller 53 coordinates the interplay between the protocol manager 51 and the presentation manager 52. More specifically, the controller 53 interacts with the protocol manager 51 to find out which frequency and presentation level to test next, and with the presentation manager 52 to administer the test. The controller 53 accumulates the results throughout the test and generates an audiogram upon completion of the test.

The controller 53 at periodic intervals may interrupt the medical protocol and request the presentation manager 52 to present a "silent" object for classification, in order to see whether the patient will report hearing it. This step, not usually taken in standard audiometry, is necessary to ensure that the patient understands and follows the rules. If the patient reports hearing sound when there are none, steps are taken ranging from repeating the test, to switching to a different presentation, to reporting a failure for that frequency in the audiogram ("unreliable"). The controller 53 preferably ensures that at least two silent object (i.e., control sounds) are being presented per frequency. If one of these control sounds is wrongly reported as being heard, then at least one additional control sound is used. In addition, the actual presentation level that was being tested when the control was failed will see additional tests being performed. In any automated version of the hearing assessment, when a given percentage of controls have failed (actual percentage set by parameter), the controller 53 automatically switches (or suggests switching) to a different type of presentation, for example, switching between the two alternative forced choice paradigm having two containers to one with a single container. If this choice is accepted, then the entire frequency is retested. If the choice is declined, then the test for that frequency is reported as unreliable in the audiogram.

The controller 53 can monitors the background noise during the hearing assessment. That is, the controller 53 examines the frequency being tested to make sure that there is no interference with the test being run. If the background noise is too high, the test can be rerun or a warning can be included in the audiogram.

The controller 53 may also be configured to interface with another hearing assessment application residing on a second computing device. For example, a first hearing assessment application operates to administer a test to a patient at one location while a second hearing assessment application is used by an audiologist monitoring the test remotely at a second location. During testing, the second hearing assessment application presents to the audiologist in real-time the presentation level for objects displayed to the patient along with the patient's response thereto. The second hearing assessment application may also present a video of the patient taking the test as captured by the first hearing assessment application. The controllers 53 of each hearing assessment application 10 can be configured to communicate with each other via a data link (e.g., WiFi, cellular, satellite, etc.).

In a profession version of the hearing assessment application, the second hearing assessment application enables the audiologist or supervising person to intervene during the administration of the test. Rather than the protocol manager 51 determining the presentation level for each presented object, the protocol manager 51 can receive input from the audiologist as to the presentation level. Should the audiologist decide to vary from the protocol being administered, the audiologist can input the desired presentation level into the second hearing assessment application. The second hearing assessment application will pass the desired presentation level to the first hearing assessment application which will in turn implement the variance in the testing protocol.

Figure 6:
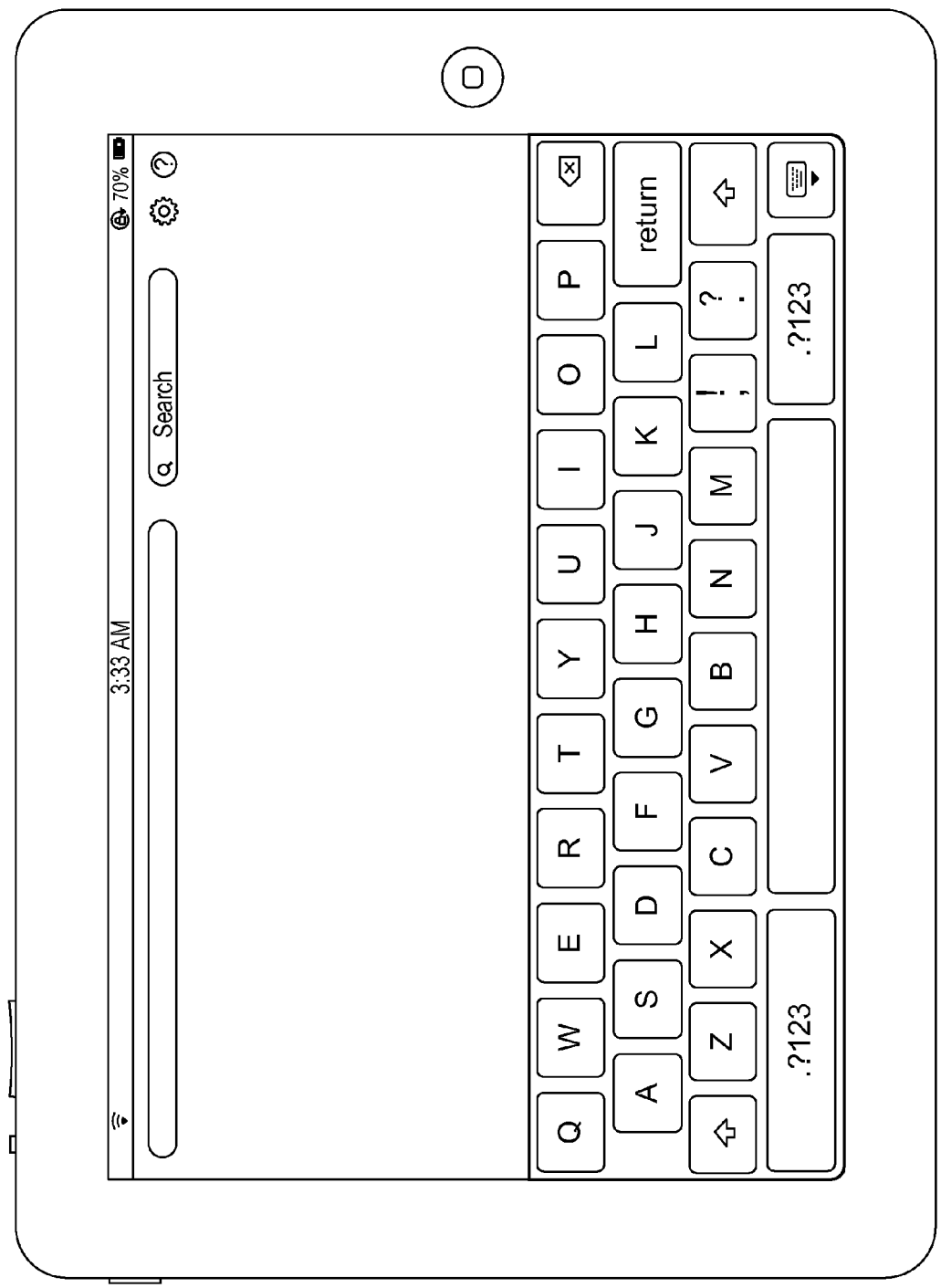
FIG. 6 is a diagram of an exemplary tablet computer.

In an exemplary embodiment, the hearing assessment application 10 resides a tablet computing device, such as the Apple iPad, as shown in FIG. 6. Touch interfaces commonly found on tablet computing devices enable even the youngest of users to interact intuitively with complex systems. Thus, the tablet appears is the preferred environment to implement a portable, automated hearing assessment application targeted at children. While reference is made to the tablet computing device, it is readily understood that the hearing assessment application 10 may be implemented on other types of computing devices, including laptop or desktop computers. In other embodiments, the hearing assessment application 10 may be implemented using professional grade audiometry equipment.

Tablet computers typically house a built-in speaker and microphone. In some embodiments, a headset, including an earphone and microphone, may be available as an accessory. The headset will connect to an audio port through a TRRS connector, and the microphone's flat frequency response makes it suitable for high-quality sound recordings. In other embodiments, the headset may be further defined as a bone transducer headset For the hearing assessment app, an appropriate scenario would include playing sounds through the built-in speakers of the tablet while using an external microphone to monitor background noise. If the framework of the tablet does not permit using the built-in route for output and the external route for input, third-party accessories could be used, such as the Cocoa framework. In the Cocoa framework, the Audio Toolbox application programming interface (API), used to read and write audio, provides a means for redirecting audio routes to select either the built-in microphone and speaker, or an external headset. The API, however, does not permit using the built-in route for output and the external route for input. One solution consists of using third-party accessories, like TouchMic's Handsfree Lapel Microphone & Adapter, to connect an external microphone and loudspeakers to the audio port. An added benefit of this solution is the ability to move the loudspeakers around to make optimal use of the room acoustics. It is however possible to use an external USB microphone with the built-in speaker using an USB adaptor. Other arrangements for interfacing an external microphone and/or speaker to the tablet are also contemplated.

Calibrating an audio system is critical before it is used to perform any scientific measurement. When a hearing test is run in an "open field", the conditions of the room (e.g., volume, texture of walls, objects at the scene) and well as the instruments used (e.g., amplified loudspeakers) are not known in advance and require a specific calibration session. Such calibration could be conducted by a specialist equipped with the necessary material, but this solution is highly unpractical. Accordingly, the hearing assessment application 10 implements a two step technique which allows a fully automated calibration on site.

In some embodiments, the hearing assessment system is comprised generally of a tablet computer hosting the hearing assessment application along with an external microphone that will be used for the room calibration. The input received through the microphone must itself be calibrated during a first calibration step. The first calibration step is done preferably inside a soundproof room or another type of acoustically controlled environment. In that setting, the microphone is plugged into the tablet computer. A calibrated sound level meter (i.e., SPL meter) is placed next to the microphone, as close to it as possible. For each tested frequency, a sound is produced by the system being calibrated. The speakers may be those integrated into the tablet computer or an external speaker system coupled to the tablet computer. During calibration, the volume of sound at a given frequency is captured and recorded by the SPL meter. Meanwhile, the power received from the microphone is also recorded, thereby determining the correspondence between the presentation level (i.e., sound volume) and the power received by the microphone. While this first calibration step may be repeated at different volumes, a single test per frequency is enough, as the power for other volumes at the same frequency can be inferred linearly from the one reading. The first calibration step can then be repeated for each frequency being tested.

Figure 7:
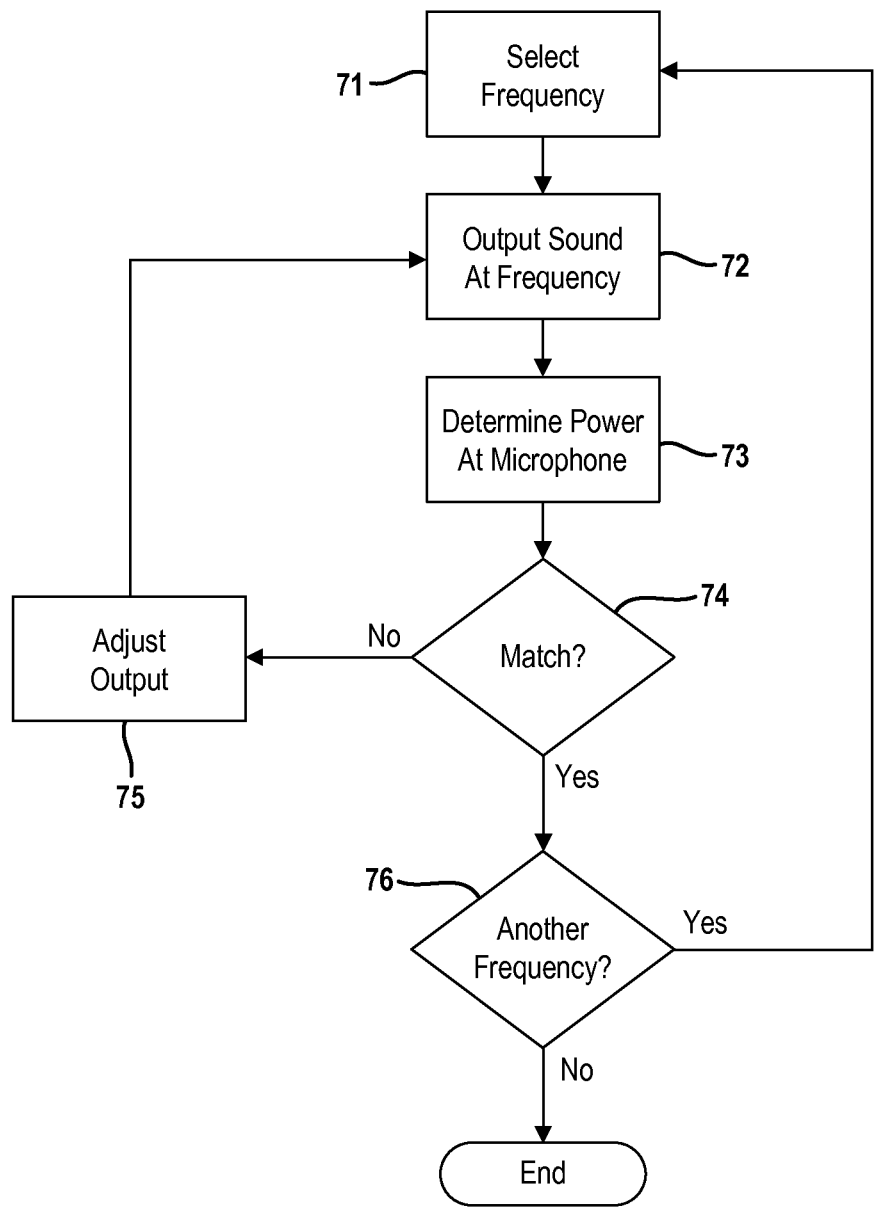
FIG. 7 is a flowchart depicting an exemplary calibration method for the hearing assessment application.

With reference to FIG. 7, the second step is an automated calibration performed at the site where the hearing assessment will take place (i.e., the testing environment). Before a hearing assessment is performed in an open field setting, a fully automated calibration is performed the hearing assessment application. If applicable, the tablet computer is hooked up to an external speaker system that will be used during the hearing assessment. The microphone that was used in the first calibration step is positioned as close as possible to where the head of the patient will be during the hearing assessment. Thus, the conditions in which the assessment will be performed are matched as closely as possible. The on-site calibration procedure is then initiated.

On-site calibration will be performed for each frequency at which hearing assessment occurs. A given frequency is selected at 71 from a listing of frequency to be tested. The system being calibrated outputs a sound 72 at the selected frequency. The system in turn determines the power input at the microphone as indicated at 73. The determined power input is compared at 74 to the expected power input which was acquired during the first calibration step. If the determined power input does not match the expected power input, the volume of the sound is adjusted at 75 until the determined power input matches the expected power input. In an exemplary embodiment, the volume of the sound is increase at predetermined increments (e.g., 5 decibels) until the determined power input matches the expected power input. If the determined power input exceeds the expected power input, then the volume of the sound can be decreased at a smaller increment, for example 1 decibel until the determined power input matches the expected power input.

Once the determined power matches the expected power at a given frequency, another frequency is selected and the process is repeated as indicated at 76 until the system has been calibrated for each frequency tested during the hearing assessment. In this way, the hearing assessment application provides a fully automated open field calibration technique.

A feasibility study of the hearing assessment application was performed. Study participants were recruited from patients presenting to the Audiology Clinic at the Children's Hospital of Eastern Ontario. The inclusion criteria for this study comprised children at least 3 years of age with normal or abnormal hearing. The exclusion criteria for the study included patients with previously diagnosed visual impairment, learning disability, or developmental delay. The aim was to enroll 80 patients into the study.

Participants completed two sequential audiometric evaluations in a double walled sound booth, one with the hearing assessment application implemented on a tablet and one with traditional play audiometry assessing warble-tone thresholds. The order in which participants performed the two assessments was determined randomly by the flip of a coin. For the sake of simplicity and speed, unmasked air conduction was the sole investigation in this study. Sound field testing was performed if the child was not amenable to wearing headphones and binaural testing was performed in all other children. Stimuli were presented using TDH-39 headphones in both the tablet and audiologist test scenarios. When sound field testing was employed, the sound booth speaker system or the tablet speakers were used. An audiologist accompanied participants in both groups to provide motivation during the assessment. The tablet computer, headphones and speakers that were used in this study were professionally calibrated to ANSI S3.6-2004 standards.

Given the novel nature of both the method and the testing hardware, no prior studies were available from which to calculate a sample size. A sample size of 80 consecutive patients was selected based on related publications comparing automated hearing tests to standard audiometry. Five additional children were recruited to allow for possible subject dropout.

The primary outcome measure consisted of warble-tone thresholds obtained by both the tablet audiometer and by standard play audiometry. Normal hearing was defined as a threshold of less than or equal to 25 dB in each of the 4 test frequencies (500, 1000, 2000 or 4000 Hz). Hearing loss was defined as audiometric thresholds greater than 25 dB in any of 4 test frequencies. Secondary outcomes related to participant performance were also documented, including time to completion as well as feedback from the audiologists. In the tablet group, test reliability was evaluated by calculating the percentage of correctly sorted silent objects Participants were excluded from analysis for (1) technical/gameplay issues (2) behavioural issues, or (3) questionable reliability, defined as incorrectly assigning greater than 50% of the silent objects. Descriptive statistics were used to summarize participant characteristics. Student's t-test with Bonferroni correction was used to compare secondary outcomes between the two groups. Preliminary evaluation of the tablet's performance was determined using a two-by-two table and calculations of sensitivity, specificity, positive and negative predictive value, and likelihood ratios positive were calculated.

A more intricate analysis of the concordance between the two hearing assessments was also performed. In order to test for overall differences between modalities (tablet versus play audiometry), a repeated measures model for the detection threshold in each ear at each frequency was fitted using linear mixed effects modeling. The model included fixed effects for testing modality (tablet versus play audiometry), frequency, and ear. In order to account for the correlation of thresholds within participants, random effects modeling was used for frequency nested within ear nested within participant.

85 consecutive patients who met the inclusion criteria were recruited into the study. 15 patients were excluded after hearing assessment, resulting in 70 subjects available for analysis. Fourteen of the 70 patients were tested using a sound field. The remainder (56) had binaural assessments for both hearing evaluations. The mean age of study participants was 5.2 years (range 3-13).

Fifteen subjects were excluded from the analysis. Four were excluded from analysis due to poor reliability (<50%). Four patients were excluded for behavioural issues that prevented successful completion of the one or both hearing assessments. Seven patients were excluded for technical issues related to test administration. Of note, 10 of 11 subjects in the latter two categories had some degree of hearing loss.

Overall, 55 patients were identified to have normal hearing by conditioned play audiometry, the traditionally accepted standard test. Of these, 52 were found to have normal hearing by tablet audiometry. The 3 remaining children scored slightly outside the defined parameters of normal hearing, namely a 30 dB threshold, in at least one frequency. This appeared to either be due to the child moving through the game too quickly or the presentation timing out before the child could make a decision.

The mean time to complete a binaural hearing test with the tablet was 152 s (SD±114 s) overall. In the group with normal hearing, the time was 109 s (SD±65 s). This increased to 317 s (SD±113 s) in children with abnormal hearing. The difference in test duration was statistically significant (p<0.0001).

53 patients in total had normal evaluation by tablet audiometry. One of these children was found to have a true mild hearing loss. This child appeared to understand the game but their results did not correlate well. The reliability score of this patient when using the table was only 75%. However he did not meet reliability criteria for exclusion (<50%). The results of the 2×2 table are summarized in table below.

| Tablet Audiometry | Play Audiometry | |
|---|---|---|
| | Abnormal Hearing | Normal Hearing |
| Abnormal Hearing | 14 | 3 |
| Normal Hearing | 1 | 52 |

Sensitivity: 93.3%
Specificity: 94.5%
Positive Predictive Value: 82.3%
Negative Predictive Value: 98.1%
Likelihood Ratio Positive: 11.5

For the repeated measures analysis, 56 participants with valid results and binaural testing were available. Patients who were tested with a sound field were excluded from this particular analysis, as ear specific information was not available, making analysis impossible.

The model showed no significant effect of testing modality (compared to audiologists, the mean tablet threshold was 0.21 dB lower (95% CI=0.18 to 0.6 dB, p=0.29). The modeling was repeated for the abnormal cases (n=15), and for the normal cases (n=41). In both cases, the model showed no significant effect of testing modality. Compared to play audiometry, the mean tablet threshold was 1.13 dB lower (95% CI=0.27 to 2.52 dB, p=0.12) and 0.12 dB higher (95% C=0.02 to 0.27 dB, p=0.10), respectively.

This disclosure describes the first trial of both a novel play algorithm using interactive audiometry and a new tablet audiometer. It is the first tablet-based, semi-automated, play audiometer to be used in a pediatric setting. The purpose of this study was two-fold, to validate the tablet audiometer as a child-friendly application for hearing assessment, as well as to compare tablet thresholds to the traditionally accepted standard play audiometry.

The data reveal that the tablet audiometer produces warble-tone thresholds that are in agreement with the accepted standard (traditional play audiometry). This was achieved with narrow confidence intervals, suggesting sufficient statistical power. Audiometric data are acquired in an efficient manner, as demonstrated by a mean test duration of approximately 2.5 minutes. Moreover, the data reveals a high specificity 94.5% with a negative predictive value (NPV) of 98.1%, denoting that tablet audiometry is a robust screening tool. The single patient who represented the 1.9% deficiency in NPV had 5 dB of agreement between his tablet and play audiometry thresholds and this is well within an acceptable margin of error. A likelihood ratio positive of 11.5 confirms the tablet audiometer's capacity to diagnose hearing loss (FIG. 3).

As the tablet audiometer is by definition an objective test, if calibrated adequately, it is not likely to be subject to issues with inter-rater reliability. However, it will be prudent in subsequent investigations to ensure strong inter-rater and test-retest reliability.

Conditioned play audiometry can often be employed with children as young as 2 years of age. The supervision and motivation given to the child by a second audiologist in the sound booth allows these very young children to be tested. In the current study, this second audiologist was present for both assessments (tablet and traditional) to maximize the successful completion of assessments, although attaining the appropriate level of support from the audiologists required training and experience.

The data suggests that using the tablet interactive audiometry method, the majority (82%, 70/85) of children as young as 3 years of age are capable of understanding the concept of the game and completing the hearing assessment. Despite the supervision of an audiologist however, some children had difficulties with the tablet audiometer. These difficulties resulted from technical deficiencies of the hardware/software (i.e. attempts to open other software, failure to understand 'drag and drop', becoming distracted by visual re-enforcements) and behaviors of the patient (i.e. boredom, poor comprehension of the game). A number of these difficulties eventually lead to the subject being excluded from the statistical analysis. Failure to complete the assessment also appeared to be more prevalent in children with abnormal hearing.

Several technical/gameplay issues were documented during data collection. In particular, children showed signs of fatigue with either test method quite quickly. During standard play audiometry, audiologists often switched games several times during standard play audiometry to keep the child engaged. By contrast, only two games were available when using the tablet, with the current software version. This stresses the importance of maintaining attention in this particular age group.

Furthermore, due to the nature of interactive audiometry, whereby the test is user-directed, action is required at each point in the decision tree. This gives the appearance of more decisions as compared to standard audiometry, where users who did not hear a sound were not required to perform an action. This was exacerbated in children with hearing loss, who were required to sort more objects in order to determine exact thresholds. For example, when testing a normal hearing individual, the minimum number of objects to complete an entire assessment was 16. This number increased to a maximum of 113 when hearing loss was present or unreliable results were being obtained. The average number of objects presented in hearing loss was 67.1 (SD±19.1). For children with normal hearing, the average was 23.8 (SD±9.45) ($p<0.0001$). Despite these challenges, the vast majority of children were engaged enough to complete the tablet hearing assessment.

Several limitations to this study are also discussed. Firstly, the majority of patients were normal hearing children. This is simply a reflection of the patient population when conducting sequential recruitment. However, a test population that is predominantly normal hearing will bias the study toward good correlation and successful completion of the relatively shorter hearing test. Second, the methods of the analysis excluded patients who were identified as having clear difficulty with the hearing assessment. This was done to ensure that the results reflect only the performance of the hardware. Although exclusion of 'difficult' patients limits the generalizability of the results, this analysis was deliberately used during this hardware validation phase. The proportion of patients excluded from analysis (18%, 15/85) insinuates a high degree of user-friendliness, especially given the potentially difficult patient population. Additionally, this emphasizes the importance of audiologist supervision, as the software is currently unable to determine if a child fully comprehends the game. Further gameplay refinement will likely increase the number of patients who are suitable candidates for tablet audiometry.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for conducting a hearing assessment of a patient, comprising the steps of:
   (i) presenting a plurality of objects on a touchscreen display of a computing device, wherein any given object from the plurality of objects is displayed at any given position on the display, and wherein each such object is capable of producing an audio output in response to a touch stimulus from the patient, and wherein the audio outputs by the objects varies in frequency and intensity amongst the plurality of objects;
   (ii) prompting the patient with a visual cue to classify each of said given objects subsequent to said touch stimulus from the patient for each of said given objects, wherein said visual cue is displayed on the display concurrently with the plurality of objects, and wherein said visual cue comprises displaying two containers on the display, whereby a first container of the two containers provides an indication that the container is for the given objects that produce audible audio output in response to the touch stimulus and the second container of the two containers provides an indication that the container is for the given objects that do not produce audible audio output in response to the touch stimulus;
   (iii) receiving touch stimulus on the touchscreen display from the patient that corresponds to the any given position of any given object on said touchscreen display;
   (iv) producing the audio output for the any given object in response to said touch stimulus;
   (v) receiving a touch input on the touchscreen display from the patient for the any given object, wherein said input comprises placement of the object by the patient in one of the first or second containers accordingly to indicate whether the audio output by the given object was audible to the patient;
   (vi) repeating steps (iii) to (v) until each of said objects in the plurality of objects has been so placed in one of the first or second containers; and
   (vii) generating, by the computing device, an audiogram for the patient based upon a totality of the input received from the patient for the plurality of objects.

2. The method of claim 1 wherein a first set of said plurality of objects is presented on the touchscreen display sequentially such that each of the any given objects from the first set of said plurality of objects is presented to the patient individually only upon placement of any previously presented given object from the first set of said plurality of objects in one of the first or second containers, and wherein the audio output from each of the any given objects from the first set is at a first frequency.

3. The method of claim 2 wherein an intensity of the audio output from the any given objects in the first set increases at a predefined increment as the given objects are presented sequentially to the patient until the audio output is indicated as audible by the patient and then the intensity of the audio output from the any given objects in the first set decreases at a predefined increment as the given objects are presented sequentially to the patient until the audio output is indicated as inaudible by the patient.

4. The method of claim 3 further comprises determining a threshold of hearing for the patient at the first frequency based upon the totality of the input received from the patient for the plurality of objects.

5. The method of claim 4 further comprising presenting on the touchscreen display a second set of said plurality of objects sequentially such that each of the any given objects from the second set of said plurality of objects is presented to the patient individually only upon placement of any previously presented given object from the second set of said plurality of objects in one of the first or second containers, and wherein the audio output produced from each of the any given objects from the second set is at a second frequency that is different from the first frequency, and wherein a first object of the any given objects in the second set of said plurality of objects produces an audio output having an intensity equal to the threshold of hearing for the patient at the first frequency.

6. The method of claim 1 wherein the plurality of objects further comprises presenting one or more random objects amongst the plurality of objects, wherein the one or more random objects are incapable of producing an audio output in response to the touch stimulus from the patient.

7. The method of claim 1 further comprises calibrating an audio system of the computing device for each frequency at which the hearing assessment will occur to account for conditions of a testing environment, said calibrating occurring prior to presenting the plurality of objects on the touchscreen display.

8. The method of claim 7 wherein calibrating the audio system of the computing device comprises the steps of:
   (i) producing, using a speaker connected to the computing device, a test audio output at one of the frequencies at which the hearing assessment will occur;
   (ii) capturing the test audio output using a microphone connected to the computing device;
   (iii) comparing an intensity of the test audio output captured by the microphone with an expected intensity of the test audio output;
   (iv) adjusting the intensity at which the speaker will produce the frequency of the test audio output when said frequency is produced during the hearing assessment such that the intensity of the test audio output matches the expected intensity of the test audio output; and
   (v) repeating steps (i) to (iv) for each frequency at which the hearing assessment will occur.

9. A computer-implemented method for conducting a hearing assessment of a patient, comprising the steps of:
   (i) sequentially presenting an object from a first set of objects at any given position on a touchscreen display of a computing device, wherein each such object from the first set of objects is capable of producing an audio output at a first frequency in response to a touch stimulus from the patient;
   (ii) prompting the patient with a visual cue to classify the sequentially presented object from the first set of objects subsequent to said touch stimulus from the patient for the object in the first set of objects, wherein said visual cue is displayed on the display concurrently with the object in the first set of objects, and wherein said visual cue comprises displaying two containers on the display, whereby a first container of the two containers provides an indication that the container is for any object that produces audible audio output in response to the touch stimulus and the second container of the two containers provides an indication that the container is for any object that does not produce audible audio output in response to the touch stimulus;

(iii) receiving the touch stimulus on the touchscreen display from the patient that corresponds to the any given position of the object on said touchscreen display;
(iv) producing the audio output at the first frequency in response to said touch stimulus;
(v) receiving a touch input on the touchscreen display from the patient for the object in the first set of objects, wherein said input indicates whether the audio output by the object was audible to the patient by placement of the object by the patient in one of the first or second containers accordingly;
(vi) sequentially presenting a further object from the first set of objects at the any given position on the touchscreen display of the computing device, wherein said object is capable of producing the audio output at a different intensity in response to the touch stimulus from the patient;
(vii) repeating steps (ii) to (vi) until each object in the first set of objects has been so placed in one of the first or second containers; and
(viii) determining a threshold of hearing for the patient at the first frequency based upon a totality of the input received from the patient in relation to the first set of objects.

10. The method of claim 9 wherein producing the audio output at a different intensity comprises increasing the intensity of the audio output between each object in the first set of objects at a predefined increment until the audio output is indicated as audible by the patient and then decreasing the intensity of the audio output between each object in the first set of objects at a defined increment until the audio output is indicated as inaudible by the patient.

11. The method of claim 9 wherein steps (i) to (viii) are repeated for a second set of objects wherein each object in the second set of objects is capable of producing the audio output at a second frequency that is different from the first frequency, and wherein a first object in the second set of objects produces the audio output having an intensity equal to the threshold of hearing for the patient at the first frequency.

12. The method of claim 9 wherein presenting the first set of objects further comprises presenting one or more random objects amongst the first set of objects, wherein the one or more random objects are incapable of producing an audio output in response to the touch stimulus from the patient.

* * * * *